US009404161B2

(12) United States Patent
Engelthaler et al.

(10) Patent No.: US 9,404,161 B2
(45) Date of Patent: Aug. 2, 2016

(54) METHOD OF DETECTING AND QUANTIFYING COCCIDIOIDES SPECIES

(71) Applicant: Translational Genomics Research Institute, Phoenix, AZ (US)

(72) Inventors: David Engelthaler, Flagstaff, AZ (US); Elizabeth Driebe, Flagstaff, AZ (US); Paul Keim, Flagstaff, AZ (US); James M. Schupp, Flagstaff, AZ (US); Erin Kelley, Flagstaff, AZ (US)

(73) Assignee: Translational Genomics Research Institute, Phoenix, AZ (US)

( * ) Notice: Subject to any disclaimer, the term of this patent is extended or adjusted under 35 U.S.C. 154(b) by 377 days.

(21) Appl. No.: 13/935,668

(22) Filed: Jul. 5, 2013

(65) Prior Publication Data

US 2014/0011693 A1 Jan. 9, 2014

Related U.S. Application Data

(60) Provisional application No. 61/668,203, filed on Jul. 5, 2012.

(51) Int. Cl.
*C12Q 1/68* (2006.01)
*C07H 21/02* (2006.01)
*C07H 21/04* (2006.01)

(52) U.S. Cl.
CPC ........ *C12Q 1/6895* (2013.01); *C12Q 2600/112* (2013.01)

(58) Field of Classification Search
None
See application file for complete search history.

(56) References Cited

PUBLICATIONS

GenBank Accession No. BH711304.1, NCBI Database, National Center for Biotechnology Information (Bethesda, MD, USA), available via url: <ncbi.nlm.nih.gov/nucgss/18801161/>, May 21, 2010.*
GenBank Accession No. CO015732.1. NCBI Database, National Center for Biotechnology Information (Bethesda, MD, USA), available via url: <ncbi.nlm.nih.gov/nucest/48522621?report=genbank&sat=1&satkey=23548274/>, Jan. 9, 2011.*
GenBank Accession No. CF814138.1. NCBI Database, National Center for Biotechnology Information (Bethesda, MD, USA), available via url: <ncbi.nlm.nih.gov/nucest/45920016//>, Jan. 9, 2011.*
Johnson, et al., "Amplification of Coccidioidal DNA in Clinical Specimens by PCR", Journal of Clinical Microbiology, May 2004, pp. 1982-1985, vol. 42. No. 5.
Binnicker, et al., "Detection of Coccidioides Species in Clinical Specimens by Real-Time PCR", Journal of Clinical Microbiology, Jan. 2007, pp. 173-178, vol. 45, No. 1.
Castonon-Oliveras, et al,. "Molecular Identification of Coccidioides Isolates from Mexican Patients", Annals of the New York Academy of Sciences, 2007, pp. 326-335.
Bialek, et al., "PCR Assays for Identification of Coccidioides posadasii Based on the Nucleotide Sequence of the Antigen 2/Proline-Rich Antigen", Journal of Clinical Microbiology, Feb. 2004, pp. 778-783, vol. 42 No. 2.

Daniels, et al., "Development of a Quantitative TaqMan-PCR Assay and Feasibility of Atmospheric Collection for Coccidioides immitis for Ecological Studies", U.S. Department of Energy, Sep. 2001, pp. 1-17.

Aguiar Cordeiro, et al., "Rapid Diagnosis of Coccdioidomycosis by nested PCR assay of Sputum", Clinical Microbiology and Infection, Apr. 2007, 430-456, vol. 13, No. 4. * See pp. 449-451 *.

* cited by examiner

*Primary Examiner* — Carla Myers

(74) *Attorney, Agent, or Firm* — Rodney J. Fuller; Booth Udall Fuller, PLC

(57) ABSTRACT

The present invention provides methods and kits that may be used to detect and quantify the presence of *Coccidioides* species. The methods include quantification real-time PCR assays, and the kits and compositions include oligonucleotides used as primers and probes.

27 Claims, No Drawings

SEQUENCE LISTING

<160> NUMBER OF SEQ ID NOS: 9

<210> SEQ ID NO 1
<211> LENGTH: 104
<212> TYPE: DNA
<213> ORGANISM: Coccidioides immitis

<400> SEQUENCE: 1
tgttaggtaa tccaactagc acctcgctca cgtgacccac atagattagc cgagattccc     60
ctttaggtag cttagtgaat gacaagcata caagtcctcc atca                    104

```
<210> SEQ ID NO 6
<211> LENGTH: 24
<212> TYPE: DNA
<213> ORGANISM: Artificial Sequence
<220> FEATURE:
<223> OTHER INFORMATION: CQ_3_R_v2a primer

<400> SEQUENCE: 6
ctgatggagg actcgtatgc ttgt                                          24

<210> SEQ ID NO 7
<211> LENGTH: 24
<212> TYPE: DNA
<213> ORGANISM: Artificial Sequence
<220> FEATURE:
<223> OTHER INFORMATION: CQ_3_R_v2b primer

<400> SEQUENCE: 7
ctgatggagg acttgtacac ttgt                                          24

<210> SEQ ID NO 8
<211> LENGTH: 24
<212> TYPE: DNA
<213> ORGANISM: Artificial Sequence
<220> FEATURE:
<223> OTHER INFORMATION: CQ_3_R_v2c primer

<400> SEQUENCE: 8
ctgatggagg aattgtatgc ttgt                                          24

<210> SEQ ID NO 9
<211> LENGTH: 24
<212> TYPE: DNA
<213> ORGANISM: Artificial Sequence
<220> FEATURE:
<223> OTHER INFORMATION: CQ_3_R_v2d primer

<400> SEQUENCE: 9
ctgatggagg acttgtatgc ttgt                                          24
```

METHOD OF DETECTING AND QUANTIFYING COCCIDIOIDES SPECIES

CROSS REFERENCE

This application is related to and claims the priority benefit of U.S. provisional application 61/668,203, filed on Jul. 5, 2012, the teachings and content of which are incorporated by reference herein.

STATEMENT REGARDING FEDERALLY SPONSORED RESEARCH

This invention was made with government support under A1076773, awarded by the National Institutes of Health. The government has certain rights in the invention.

FIELD OF THE INVENTION

The present invention provides methods and kits for specifically detecting and quantifying *Coccidioides* in a sample.

BACKGROUND OF THE INVENTION

Coccidioidomycosis is caused by infection with *Coccidioides immitis* or *Coccidioides posadasii* (collectively "*Coccidioides*"). *C. immitis* and *C. posadasii* are the fungal etiologic agents of coccidioidomycosis (a.k.a., Valley Fever) and are endemic to arid soils of the southwest United States, as well as parts of Mexico, and Central and South America. Primary hosts acquire *Coccidioides* via inhalation of aerosolized arthroconidia upon soil disruption. Coccidioidomycosis most commonly causes a progressive pulmonary infection in humans and other vertebrate hosts but also can disseminate to other body parts including the skin, brain, bone, and meninges. This disseminated secondary coccidioidomycosis often is severe and can result in patient death. However, in cases where infection is resolved, patients usually acquire a specific and lifelong immunity to the fungus.

Coccidioidomycosis infection rates have increased dramatically in the last decade with the State of Arizona documenting the number of reported cases per 100,000 people having increased from 20.8 in 1997 to 186.0 in 2010. Increased physician awareness and testing likely accounts for a portion of this case increase. An additional cause for this increase may be influxes of immunologically naive individuals into Arizona. A significant number of individuals from outside the *Coccidioides* endemic region migrate annually to the desert southwest and are at greater risk for developing coccidioidomycosis, even after returning to their respective homes. These infections, therefore, are likely to escape or confound diagnosis in non-endemic regions.

While Real Time PCR based assays have been developed that can help clinicians identify *Coccidioides* as a cause of illness, these assays have lacked needed detection sensitivity and do not accurately detect or quantify the load of *Coccidioides* organisms in an infection.

BRIEF SUMMARY OF THE INVENTION

Provided herein is a method of determining the presence or absence of *Coccidioides* in a DNA-containing sample. The general method comprises the steps of: (1) adding a first and a second oligonucleotide each capable of binding SEQ ID NO. 1 to a mixture comprising the DNA-containing sample, wherein the first oligonucleotide preferably includes a sequence selected from the group consisting of SEQ ID NO.

3, SEQ ID NO. 4, SEQ ID NO. 5, and homologs thereof having at least 80% sequence identity and complementarity under similar stringency, and wherein the second oligonucleotide preferably includes a sequence selected from the group comprising SEQ ID NO. 6, SEQ ID NO. 7, SEQ ID NO. 8, SEQ ID NO. 9, and homologs thereof having at least 80% sequence identity and complementarity under similar stringency; (2) subjecting the mixture to conditions that allow amplification of nucleic acid comprising the first oligonucleotide; (3) obtaining a result indicating nucleic acid amplification comprising the first oligonucleotide; and (4) determining the presence or absence of *Coccidioides* in the DNA-containing sample based on the result. In some examples, the result obtained by the general method comprises a Ct value. In the general method, the first oligonucleotide is capable of hybridizing with complements of SEQ ID NO. 3, and the second oligonucleotide is capable of hybridizing with complements of SEQ ID NO. 6 in the mixture.

The general method as set forth above may further comprise the step of adding a third oligonucleotide to the mixture, wherein the third oligonucleotide binds to its complement included in the amplification products by the first and second oligonucleotides. The third oligonucleotide preferably includes a sequence selected from the group consisting of SEQ ID NO. 2 and homologs thereof having at least 80% sequence identity and complementarity under similar stringency. In the general method, at least one of the first, the second and the third oligonucleotides comprises a label. For some examples, the label may comprise a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In one example, the third oligonucleotide comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In some preferred embodiments, when at least two or all of the first, second, and third oligonucleotides include labels, the labels are preferably different for the at least two and preferably for each of the respective oligonucleotides.

The general method as provided may further comprise the step of isolating DNA from the DNA-containing sample. The sample may comprise an environmental sample or may be derived from a subject. In preferred forms, the subject is selected from the group consisting of a human, a companion animal, a livestock animal, and a wild animal species.

The general method may include the step of subjecting the DNA from the sample to a reverse transcription step to generate cDNA and then detecting and/or quantifying RNA. These steps can be done alone or in addition to detecting and/or quantifying *Coccidioides* in the DNA-containing sample.

Also provided is a method of quantifying *Coccidioides* in a DNA-containing sample. The method comprises the steps of: (1) adding a first and a second oligonucleotide, each capable of binding SEQ ID NO. 1, to a mixture comprising the DNA-containing sample, wherein the first oligonucleotide includes a sequence selected from the group consisting of SEQ ID NO. 3, SEQ ID NO. 4, SEQ ID NO. 5 and homologs thereof having at least 80% sequence identity and complementarity under similar stringency, wherein the second oligonucleotide includes a sequence selected from the group comprising SEQ ID NO. 6, SEQ ID NO. 7, SEQ ID NO. 8, SEQ ID NO. 9, and homologs thereof having at least 80% sequence identity and complementarity under similar stringency; (2) subjecting the mixture to conditions that allow amplification of nucleic acid amplification comprising the first oligonucleotide; (3) obtaining a first result indicating nucleic acid amplification and *Coccidioides* quantification comprising the first oligonucleotide. The quantification method may further comprise the step of calculating *Coccidioides* quantification based on the first result in comparison to a reference result. In some examples, the reference result is obtained by the same quantification method using a DNA-containing sample having a known quantity of *Coccidioides*. In some other examples, the reference result is predetermined. Sometimes, each of the first and the reference result comprises a Ct value. The Ct value can be compared to a theoretic or empirically determined quantitative value based upon known amplification kinetics, genome target, copy number, or with standard quantitative controls. In the quantification method, the first oligonucleotide is capable of hybridizing with complements of SEQ ID NO. 3, and the second oligonucleotide is capable of hybridizing with complements of SEQ ID NO. 6, under stringent conditions.

The quantification method may further comprise the step of adding a third oligonucleotide to the mixture, wherein the third oligonucleotide binds to its complement included in the amplification products by the first and second oligonucleotides. In one example, the third oligonucleotide includes a sequence selected from the group consisting of SEQ ID NO. 2 and homologs thereof having at least 80% sequence identity and complementarity under similar stringency. In the quantification method, at least one of the first and the second oligonucleotides comprises a label. In some preferred embodiments, at least two or at least three of each of the first, second, and third oligonucleotides include labels. Preferably, each respective label for each respective oligonucleotide is different. In some examples, the label comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ. In one example, the third oligonucleotide comprises a fluorescent label selected from the group consisting of FAM, dR110, 5-FAM, 6FAM, dR6G, JOE, HEX, VIC, TET, dTAMRA, TAMRA, NED, dROX, PET, BHQ+, Gold540, MGB-NFQ, and LIZ.

The quantification method may further comprise the step of isolating DNA from the DNA-containing sample. In some examples, the sample comprises an environmental sample. In other examples, the sample is derived from a subject. Preferably the subject is selected from the group consisting of a human, a companion animal, and a livestock animal.

As noted above, the DNA from the DNA-containing sample can undergo reverse transcription to generate cDNA. In such embodiments, RNA can be detected and quantified in addition to or separately from the DNA. When RNA is detected and/or quantified, the sensitivity of the assay can be increased. Advantageously, when RNA is used, it can only be present when live material is present. Thus, identification with RNA would indicate active infection.

Further provided is a kit that facilitates the detection of *Coccidioides* in a DNA-containing sample. The kit preferably comprises a first oligonucleotide capable of hybridizing with complements of SEQ ID NO. 3; and an indicator of the resulting hybridization that signifies when the sample contains *Coccidioides*. The first oligonucleotide of the kit is preferably selected from the group consisting of SEQ ID NO. 3, SEQ ID NO. 4, SEQ ID NO. 5, and homologs thereof having at least 80% sequence identity and complementarity under similar stringency. With the first oligonucleotide provided as such, the kit further comprises a second oligonucleotide capable of hybridizing with complements of SEQ ID NO. 6, under stringent conditions. In some examples, the second oligonucleotide is preferably selected from the group consisting of SEQ ID NO. 6, SEQ ID NO. 7, SEQ ID NO. 8, SEQ ID NO. 9, and homologs thereof having at least 80% sequence identity and complementarity under similar stringency. The kit may further comprise a third oligonucleotide capable of binding to its complement included in the amplification products by the first and second oligonucleotides. In one example, the third oligonucleotide includes sequence selected from the group consisting of SEQ ID NO. 2 and homologs thereof having at least 80% sequence identity and complementarity under similar stringency.

The kit, as provided herein, may further comprise a device for collecting a sample. The result indication of the kit comprises a Ct value. In some examples, the indication or indicator comprises a positive control, or it comprises a writing, or it comprises an amplification plot.

The kit as provided herein may further comprise a construct comprising a sequence selected from SEQ ID NO. 2, SEQ ID NO. 3, SEQ ID NO. 4, SEQ ID NO. 5, SEQ ID NO. 6, SEQ ID NO. 7, SEQ ID NO. 8 and SEQ ID NO. 9; wherein the construct is provided at a first known concentration; and wherein the construct is useful for *Coccidioides* quantification in a sample. Sometimes, the construct is further provided at a second known concentration. In this situation, the kit may further comprise an indication of a dilution scheme that yields a plurality of known concentrations of the construct.

The kit may also be designed for RNA detection and/or quantification.

Advantageously, the copia-like retrotransposon is well suited for the methods of the present invention due to the fact that it is highly repeated and specific for *Coccidioides*. Thus, the present invention provides for total nucleic acid detection (DNA and/or RNA), which results in greater sensitivity (detecting genome and gene transcripts).

Other aspects and iterations of the invention are described in more detail below.

DETAILED DESCRIPTION OF THE INVENTION

The present invention discloses assays, methods and kits designed to detect and quantify total *Coccidioides* sp in a sample. This invention provides a genomic target specific to *Coccidioides* sp, including *C. immitis* and *C. posadasii*. Advantageously, this target can be detected and quantified using the information provided herein. A real-time quantitative Polymerase Chain Reaction (real-time qPCR) based assay, providing a straightforward, highly sensitive and specific assay system for rapidly detecting *Coccidioides* in a sample, is provided based on the genomic target disclosed herein.

I. Species or Strain Specific Sequences

Species or strain specific sequences are sequences unique to the species or strain, that are not shared by other previously characterized species or strains. The species specific sequences identified in *C. immitis* and *C. posadasii* often differ only by a single nucleotide, which is called SNP (single nucleotide polymorphism). The strain specific SNP, is also called allelic identification herein, signifies the identity of *C. immitis* or *C. posadasii*. The concept of "allele" or "allelic" is detailed below. Because of the degree of identity between *C. immitis* or *C. posadasii* and the presence of highly repeated and specific target sequence in each of these species, the single assay of the present invention can comprehensively, accurately, and sensitively detect *Coccicioides*.

When a particular species or strain specific sequence is identified, probes or primers may be designed based on any part of that sequence. The probes or primers may also be the entirety of that sequence. The primers or probes designed according to a particular species or strain sequence, or alleles thereof, may also be represented in degenerate form, or comprise chemically modified nucleic acids, or any other components that facilitate the identification of the identifying sequence of a strain or species. The concept of a sequence identified to be specific to a species or strain further encompasses nucleic acid sequences that are less than 100% identical to the specific sequence, but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence or allele thereof may still be encompassed by the invention if it is capable of binding to its complementary sequence and/or facilitating nucleic acid amplification of a desired target sequence.

An allele includes any form of a particular nucleic acid that may be recognized as a form of existence of a particular nucleic acid on account of its location, sequence, modification, or any other characteristics that may identify it as being a particular existing form of that particular nucleic acid. Alleles include, but need not be limited to, forms of a nucleic acid that include point mutations, deletions, single nucleotide polymorphisms (SNPs), inversions, translocations, heterochromatic insertions, and differentially methylated sequences relative to a reference gene, whether alone or in combination. When a particular nucleic acid is a gene, the allele of this particular gene may or may not produce a functional protein; the functional protein thereof may or may not comprise a silent mutation, or frame-shift mutation. The different alleles of a particular gene may each produce a protein with altered function, localization, stability, dimerization, or protein-protein interaction; and may have overexpression, underexpression or no expression; may have altered temporal or spacial expression specificity. The presence or absence of an allele may be detected through the use of any process known in the art, including using primers and probes designed accordingly for PCR, sequencing, or hybridization analyses. An allele may also be called a mutation or a mutant. An allele may be compared to another allele that may be termed a wild type form of an allele. In some cases, the wild type allele is more common than the mutant.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single-stranded for maximum efficiency in amplification. Alternatively, the primer is first treated to ensure that it is single-stranded before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Oligonucleotides, such as a probe or primer, containing a sequence complementary to a sequence specific to a *Coccidioides* species or strain will typically not hybridize to the corresponding portion of the genome of other species or strains under stringent conditions. Understood by those skilled in the art, for example, highly stringent hybridization conditions are equivalent to: 5×SSPE, 0.5% SDS, 5× Denhardt's reagent and 100 µg/ml denatured salmon sperm DNA at 42° C. followed by washing in a solution comprising 0.1× SSPE, 1.0% SDS at 42° C. when a probe of about 500 nucleotides in length is employed, and washed with 2×SSC, 0.1% SDS followed by 0.1×SSC, 0.1% SDS. Stringent conditions in PCR reactions may be controlled by temperature or by the concentration of certain salt in the buffer.

Primers and probes that are designed based on strain specific genes, allelic discriminative nucleic acid, or alleles thereof, are often used to screen samples to specifically and selectively detect the presence or absence of a particular species or strain of a bacteria, fungus, virus, or a pathogen thereof. The detection using primers and probes may be through various methods including PCR-based (polymerase chain reaction-based) methods such as real-time PCR, quantitative PCR, quantitative real time PCR; allele specific ligation; comparative genomic hybridization; sequencing; and other methods known in the art. One aspect of the present invention provides primers based on *Coccidioides* specific sequence for quantitative PCR assays comprising one or more specific primer sets and probes to detect the presence of *Coccidioides* DNA.

As to probes, they may be used for single probe analysis or multiplex probe/primer combined Real Time PCR and/or quantitative PCR (qPCR) analysis. Oligonucleotide probes complementary to a selected sequence within the target sequence defined by the amplification region by the primers may be designed. In one exemplary example, oligonucleotide probes facilitating Real Time-PCR/qPCR product detection are complementary to a selected sequence within the target sequence downstream from either the upstream or downstream primer. Therefore, these probes hybridize to an internal sequence of the amplified fragment of a targeted sequence.

Many assays detecting the presence of a target can also quantify the amount of the target in a given sample. In particular, when there is only one copy of the identified strain specific genes, alleles thereof, or other allelic discriminative nucleic acid in a fungal genome, the primers and probes designed to specifically and selectively detect the presence or absence of such single copy target may be further used to quantify the amount of *Coccidioides* spp in a sample. In one embodiment, the *Coccidioides* quantitative diagnosis assay ("CocciDxQ" hereafter) as provided herein is used to quantify *Coccidioides* via a region that is associated with copia-like retrotransposon family protein found in *Coccidioides posadasii* C735 delta SOWgp (GenBank Accession XM_003069703.1; SEQ ID NO:1—TGTTAGGTAATC-CAACTAGCACCTCGCTCACGTGACCCA-CATAGATTAGCCGAGATT CCCCTTTAGGTAGCT-TAGTGAATGACAAGCATACAAGTCCTCCATCA) specific to *Coccidioides*. In another embodiment, the CocciDxQ assay is a real-time PCR that employs a probe and a multiplex set of forward primers and reverse primers that target part or all of the target sequence represented by SEQ ID NO: 1. In one embodiment, the probe is labeled with fluorescence. In another embodiment, the probe comprises a 6FAM and an MGB-NFQ label. In one embodiment the probe comprises sequence represented by SEQ ID NO: 2 or homologs of SEQ ID NO: 2 with at least 80% identity, more preferably 90%, still more preferably 91%, even more preferably 92%, still more preferably 93%, even more preferably 94%, still more preferably 95%, even more preferably 96%, still more preferably 97%, even more preferably 98%, still more preferably 99%, and most preferably 99.8% or more identity and complementarity under similar stringency. In one embodiment, the CocciDxQ assay as disclosed herein comprises at least one forward primer and at least one reverse primer comprising primer sequences represented by SEQ ID NOs in Table 1 or homologs of SEQ ID NOs in Table 1 with at least 80% identity and complementarity under similar stringency. In one embodiment, the forward primers comprise one or more degenerative primers. In another embodiment, the reverse primers comprise one or more degenerative primers. In yet another embodiment, both the forward primers and the reverse primers comprise one or more degenerative primers. In some embodiments, the CocciDxQ assay may comprise more than 1 forward primer and more than 1 reverse primer. For example, the CocciDxQ assay may comprise two, three, four and more primers; as such, the CocciDxQ assay may comprise two forward primers and one reverse primer, or two forward primers and two reverse primers, or three forward primers and one reverse primer. In one embodiment, the CocciDxQ assay comprises three forward primers and four reverse primers represented by SEQ ID NOs: 3-9 (Table 1).

TABLE 1

| Probe Name | Probe Sequence 5' to 3' | SEQ ID NO |
|---|---|---|
| CQ_3_probe | ACCCACATAGATTAGC | SEQ ID NO: 2 |
| Forward Primer Name | Forward Primer Sequence to 3' | |
| CQ_3_F_v2a | GTGTTAGGTAGTCCAACTAGCACCT | SEQ ID NO: 3 |
| CQ_3_F_v2b | GTGTTAGGTAATCCAACCAGCACCT | SEQ ID NO: 4 |
| CQ_3_F_v2c | GTGTTAGGTAATCCAACTAGCACCT | SEQ ID NO: 5 |
| Reverse Primer Name | Reverse Primer Sequence 5'to 3' | |
| CQ_3_R_v2a | CTGATGGAGGACTCGTATGCTTGT | SEQ ID NO: 6 |
| CQ_3_R_v2b | CTGATGGAGGACTTGTACACTTGT | SEQ ID NO: 7 |
| CQ_3_R_v2c | CTGATGGAGGAATTGTATGCTTGT | SEQ ID NO: 8 |
| CQ_3_R_v2d | CTGATGGAGGACTTGTATGCTTGT | SEQ ID NO: 9 |

The provided assay can detect less than one genomic DNA molecule per microliter of DNA, which sensitivity is imparted by high genomic copy number of the target gene of at least 85 copies/genome.

Further illustrations of various aspects of the invention are detailed below.

II. Methods for Detecting *Coccidioides* Using Species Specific Genomic Target Sequences Methods that can be used to identify strain or species specific nucleic acids and alleles thereof, and biomarkers derived from transcriptional and translational products of the strain or species specific nucleic acids and the alleles thereof, include PCR, Real Time-PCR, hybridization, sequencing and any combination of the above methods. In one embodiment, the presence of the PCR or Real Time-PCR products in an assay may indicate the presence of *Coccidioides* species or one or more strains thereof. In one embodiment, the PCR or Real Time-PCR products may be further identified or differentiated by hybridization performed either simultaneously with or subsequently to the PCR reactions. In another embodiment, the PCR or Real Time-PCR products may be sequenced to ascertain the existence of a particular allele indicative of the identity of *Coccidioides* species or one or more strains thereof in a sample.

A nucleic acid may be added to a sample by any of a number of methods, including manual methods, mechanical methods, or any combination thereof. The presence of the allele may be signified by any of a number of methods, including amplification of a specific nucleic acid sequence, sequencing of a native or amplified nucleic acid, or the detection of a label either bound to or released from the nucleic acid. Addition of the nucleic acid to the sample also encompasses a sample absent of the target allele to which the nucleic acid has specificity.

(a) PCR

Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as ϕ29, whole genome PCR, in vitro transcription with Klenow or any other RNA polymerase, or any other method by which copies of a desired sequence are generated.

With PCR, it is possible to amplify a single copy of a specific target sequence in genomic DNA to a level detectable by several different methodologies, such as hybridization with a labeled probe; incorporation of biotinylated primers followed by avidin-enzyme conjugate detection; incorporation of $^{32}$P-labeled deoxynucleotide triphosphates—dCTP or dATP—into the amplified segment. In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR.

Either primers or primers along with probes, as described above, will allow a quantification of the amount of specific template DNA present in the initial sample. In addition, RNA may be detected by PCR analysis by first creating a DNA template from RNA through a reverse transcriptase enzyme. In some aspects of the invention, the allele may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g., Applied Biosystems™ 7900HT real-time PCR platform (Applied Biosystems, Carlsbad, Calif.), Roche's 480 LightCycler (Roche, Basel, Switzerland), the ABI Prism 7700 sequence detector (Applied Biosystems, Carlsbad, Calif.) using 96-well reaction plates, GENEAMP PC System 9600 or 9700 (Applied Biosystems, Carlsbad, Calif.) in 9600 emulation mode followed by analysis in the ABI Prism Sequence Detector or TAQMAN LS-50B PCR Detection System (Applied Biosystems, Carlsbad, Calif.). The labeled probe facilitated multiplex Real Time-PCR/PCR can also be performed in other real-time PCR systems with multiplexing capabilities.

In some forms of PCR assays, quantification of a target in an unknown sample is often required. Such quantification is often in reference to the quantity of a control sample. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithms.

The algorithm for Ct values in Real Time-PCR calculates the cycle at which individual PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software (Roche, Basel, Switzerland) calculates the second derivatives of entire amplification curves and determines where this value is at its maximum. By using the second-derivative algorithm, data obtained are more reliable and reproducible, even if fluorescence is relatively low.

(b) Hybridization

In addition to PCR, genotyping analysis may also be performed using a probe that is capable of hybridizing to a nucleic acid sequence of interest. The term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids. A single molecule that contains pairing of complementary nucleic acids within its structure is said to be "self-hybridized."

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology, or complete homology and thus identical. "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence, one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding, or hybridization, of a sequence that is completely homologous to a target under conditions of low stringency. This is not to say that conditions of low stringency are such that non-specific binding is permitted; low stringency conditions require that the binding of two sequences to one another be a specific and selective interaction. The absence of non-specific binding may be tested by the use of a second target which lacks even a partial degree of complementarity, for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components, for example, the presence or absence of formamide, dextran sulfate, polyethylene glycol, are considered and the hybridization solution may be varied to generate conditions of low stringency hybridization different from, but equivalent to, the above listed conditions. In addition, conditions are known in the art that promote hybridization under conditions of high stringency, for example, increasing the temperature of the hybridization and/or wash steps, the use of formamide in the hybridization solution, etc.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize, or is the complement of, the single-stranded nucleic acid sequence under conditions of low to high stringency as described above.

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41$ (% G+C), when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

A "biological sample" refers to a sample obtained from eukaryotic source. Examples of eukaryotic sources include animals, for example, a human, a livestock animal, a rabbit, a game animal, and/or a member of the family Muridae (a murine animal such as rat or mouse). A biological sample may include blood, urine, feces, or other materials from a eukaryotic source. A biological sample can be, for instance, in the form of a single cell, in the form of a tissue, or in the form of a fluid.

Probes for hybridization may comprise nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide, as described herein.

Under some circumstances, methods of detecting a gene or an allele may involve assessing their expression level through their transcriptional or translational products such as a RNA or protein molecules. The expression of a gene or an allele may be assessed by any of a number of methods used currently in the art and yet to be developed. Examples include any nucleic acid detection method, including the following nonlimiting examples, microarray analysis, RNA in situ hybridization, RNAse protection assay, Northern blot. Other examples include any process of detecting expression that uses an antibody including the following nonlimiting examples, flow cytometry, immunohistochemistry, ELISA, Western blot, Northwestern blot, and immunoaffinity chromatograpy. Antibodies may be monoclonal, polyclonal, or any antibody fragment, for example, Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

In some aspects of the invention, the presence of an allele may be established by binding to probes in a media or on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subjected to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye from differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof, or any other compound that may be differentially detected. The label may also include one or more fluorescent dyes optimized for use in genotyping. Examples of such dyes include, but are not limited to: dR110, 5-FAM, 6FAM, dR6G, JOE, HEX, VIC, TET, dTAMRA, TAMRA, NED, dROX, PET, BHQ+, Gold540, and LIZ. In one embodiment, the probe comprising SEQ ID NO: 2 is labeled with 6FAM at 5' end and MGB-NFQ at 3' end.

(c) Sequencing

Methods of detecting the presence of a gene or an allele further include, but are not limited to, any form of DNA sequencing including Sanger, next generation sequencing, pyrosequencing, sequencing by ligation, sequencing by synthesis, single molecule sequencing, pooled, and barcoded DNA sequencing or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides, or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfurylase enzyme converts pyrophosphate into ATP which, in turn, catalyzes the conversion of luciferin to oxyluciferin which results in the generation of visible light that is then detected by a camera.

In sequencing by ligation, such as, SOLID™ sequencing, the molecule to be sequenced is fragmented and used to prepare a population of clonal magnetic beads, in which each bead is conjugated to a plurality of copies of a single fragment with an adaptor sequence, and alternatively, a barcode sequence. The beads are bound to a glass surface. Sequencing is then performed through 2-base encoding.

In sequencing by synthesis, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

III Kits.

Kits that facilitate methods of detecting a strain or species specific sequence may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication that links the output of the kit to a particular result. For example, an indication may be one or more sequences or that signify the identification of a particular fungal phylum, class, order, family, genus species, subspecies, strain or any other delineation of a group of fungi. An indication may include a Ct value, wherein exceeding the Ct value indicates the presence or absence of an organism of interest. A kit may contain a positive control. A kit may contain a standard curve configured to quantify the amount of fungus present in a sample. An indication includes any guide that links the output of the kit to a particular result. The indication may be a level of fluorescence or radioactive decay, a value derived from a standard curve, or from a control, or any combination of these and other outputs. The indication may be printed on a writing that may be included in the kit or it may be posted on the Internet or embedded in a software package.

EXAMPLES

Various embodiments of the present teachings can be illustrated by the following non-limiting examples. The following embodiments and examples are illustrative, and are not intended to limit the scope of the claims.

Example 1

Method and Material

The assay employs TaqMan MGB 6FAM fluorescent probe and a multiplex set of three forward primers and 4 reverse primers (Table 1 above). The assay reactions can be performed using Real Time PCR Mastermix of choice, but has been optimized for use with Quanta Biosciences PerfeCTa® qPCR FastMix®, UNG, ROX™. Thermocycling conditions consist of UNG activation for 3 min at 50° C. followed by 10 min Taq Polymerase activation at 95° C. and 50 PCR cycles of 15 s at 95° C. and 1 min at 60° C. Each reaction produced an amplification plot yielding a cycle-threshold (Ct) value directly proportional to the initial concentration of DNA in the reaction.

Example 2

Sensitivity and Specificity of the Cocci Quantitative Diagnosis Assay (I) Determining Limit of Detection The Limit of Detection (LOD), also called the Detection Limit or Lower Limit of Detection, is the lowest quantity of a substance that can be distinguished from the absence of that substance (i.e., a blank value) within a stated confidence limit. LOD is hereby used to describe the sensitivity of quantitative assays. The assay target region, a multi-copy target having the advantage of being detected at low levels in comparison to a single-copy target was utilized in the LOD test. Although the copy number of assay target region in *Coccidioides* isolates, including *C. immitis* and *C. posadasii*, varies, however, the average number of target copies in a *Coccidioides* genome is estimated at 66. Therefore, the ability of an assay in detecting the target region provides a method for relative quantification of *Coccidioides* fungal load.

The analytical LOD of the CocciDxQ assay is 15 target copies/ul (Table 2). This translates to less than one genome/ul. Genomic DNA was quantified and limiting serial dilutions were created to test the LOD. Dilutions were queried across the CocciDxQ assay with 20 replicates each. Finally, to establish the LOD, dilutions for which at least 19 of 20 replicates amplified were further evaluated by testing 64 replicates and exhibited at least 95% amplification (61/64 amplification ratio). Results are shown in Table 2.

TABLE 2

Determination of Limit of Detection of CocciDxQ assay:

| Dilution of Target Copies/1 ul | Amplification Ratio of 20 Replicate Screen | Amplification Ratio of 64 Replicate Screen | Mean Ct | CocciQuant Limit of Detection (Target Copies/1 ul) |
|---|---|---|---|---|
| 25 | 20/20 | 62/64 | 31.08 | 15 copies/1 ul |
| 15 | 20/20 | 62/64 | 31.72 | (Ct = 31.72, Ct |
| 10 | 19/20 | 58/64 | 32.61 | std. dev. = 0.77) |
| 5 | 17/20 | N/A | 36.93 | |
| 3 | 14/20 | N/A | 37.74 | |
| 1 | 6/20 | N/A | 37.80 | |
| 0.1 | 2/20 | N/A | 36.45 | |
| 0.01 | 3/20 | N/A | 38.08 | |

The analytical LOD of the assay is 15 target copies/ul, which means if the copy number/1 μl of the genomic target in a sample is lower than 15, the CocciDxQ assay may not be sensitive enough to either reliably detect the presence or absence of the target, nor a reliable calculation of the copy number of a target DNA in the sample. However, the sensitivity of the CocciDxQ assay is imparted by high genomic copy number of the target region, an area associated with a copia-like retrotransposon, which is 85 copies/genome. Thus, the CocciDxQ assay as disclosed herein can detect equivalents to less than one genomic DNA molecule per microliter of DNA, which is highly sensitive.

(2) Assay Specificity

To further illustrate the specificity of the CocciDxQ assay, the assay was tested against a panel of 89 diagnostic differential DNA's including differential diagnostic isolates and near neighbor or background isolates to detect any cross reactivity. All assay results were negative (see Table 3), indicating the sample species doesn't contain *C. immitis* and *C. posadasii* specific sequence amplifiable using the CocciDxQ assay comprising probe and primer sets in Table 1, and thus proved the assay specificity.

TABLE 3

List of DNA that the CocciDxQ Assay was screened across.

| | |
|---|---|
| Human gDNA | *Streptococcus pneumoniae* |
| *Burkholderia pseudomallei* | *Staphylococcus capitis* |
| *Streptococcus lactis* | *Mycoplasma pneumoniae* |
| *Streptococcus oralis* | *Enterobacter cloacae* |
| *Haemophilus Influenzae* | *Streptococcus mitis* |
| *Acinetobacter baumanni* | *Streptococcus salivarius* |
| *Streptococcus thermophilus* | Methicillin Resistant *Staphylococcus aureus* |
| *Streptococcus anginosus* | Methicillin Sensitive *Staphylococcus aureus* |
| *Streptococcus mutans* | *Micrococcus* sp |
| *Staphylococcus arlettae* | *Chryseobacterium indologenes* |
| *Staphylococcus chonii* | *Klebsiella oxytoca* |
| *Staphylococcus equorum* | *Enterococcus faecalis* |
| *Staphylococcus gallinarum* | *Haemophilus parainfluenzae* |
| *Staphylococcus hominis* | *Achromobacter xylosoxidans* |
| *Staphylococcus kloosii* | *Staphylococcus xylosus* |
| *Staphylococcus lugdunensis* | *Klebsiella pneumoniae* |
| *Streptococcus gordonii* | *Moraxella catarrhalis* |
| *Streptococcus equi* | *Staphylococcus epidermidis* |
| *Streptococcus uberis* | *Staphylococcus haemolyticus* |
| *Providencia stuartii* | *Streptococcus pyogenes* |
| *Corynebacterium jeikeium* | *Acremonium strictum* |
| *Stenotrophomonas maltophilia* | *Bacillus anthracis* |
| *Fusobacterium nucleatum* | *Brucella abortus* |
| *Corynebacterium diphtheriae* | *Candida famata* |
| *Porphyromonas gingivalis* | *Candida haemulonii* |
| *Cryptococcus neoformans* | *Candida lusitaniae* |
| *Mycobacterium avium* | *Chaetomium globosum* |
| *Aspergillus niger* | *Escherícha coli* |

TABLE 3-continued

List of DNA that the CocciDxQ Assay was screened across.

| | |
|---|---|
| *Penicillium marneffei* | *Francisella tularensis* |
| *Eikenella corrodens* | *Fusarium solani* |
| *Enterobacter aerogenes* | *Geotrichum candidum* |
| *Staphylococcus saprophyticus* | *Histoplasma capsulatum* |
| *Pseudomonas aeruginosa* | *Legionella pneumophila* |
| *Neisseria meningitidis* | *Listeria monocytogenes* |
| *Entercoccus faecium* | *Paecilomyces variotii* |
| *Neisseria gonorrhoeae* | *Pichia ohmeri* |
| *Burkholderia cepacia* | *Rhizopus oryzae* |
| *Bordetella bronchiseptica* | *Salmonella typhimurium* |
| *Candida albicans* | *Sporothrix schenckii* |
| *Bacteroides fragilis* | *Trichosporon asteroides* |
| *Bacteroides uniformis* | *Trichosporon faecale* |
| *Streptococcus agalactiae* | *Trichosporon ovoides* |
| *Candida glabrata* | *Uncinocarpus reesi* |
| *Candida parapsilosis* | *Burkholderia ubonensis* |
| *Candida tropicalis* | |

The CocciDxQ assay was further screened across isolates containing *Coccidioides* spp. using DNA extracts or whole genome amplifications of DNA extracts, and the assay detected *Coccidioides* spp. in 559 out of 560.

Example 3

CocciDxQ Assay for Clinical Specimen

Clinical specimens suspected having *Coccidioides* spp. were tested with the CocciDxQ assay. DNA was extracted from those specimens which were blood, sputum, saliva, urine, or sputum-LSA. The test results provided in Table 4 show that sputum samples provide DNA suitable for the CocciDxQ assay.

TABLE 4

CocciDxQ test using DNA of clinical samples

| Specimen Type | Amplification rate (# of samples tested) | Mean Ct |
|---|---|---|
| Blood | 0 (13) | n/a |
| Sputum | 1 (6) | 37.2 |
| Saliva | 0 (14) | n/a |
| Urine | 0 (13) | n/a |
| Sputum-LSA | 16 (25) | 27.5 |

DNA and RNA extracted from pleural fluid specimens were also tested using the CocciDxQ assay. The Real-Time PCR results are shown in Table 5.

TABLE 5

CocciDxQ assay for clinical pleurial fluid specimens

| Sample | CocciDxQ Ct on DNA | CocciDxQ Ct on RNA |
|---|---|---|
| 3838H | Neg | 38.0 |
| 0681J | Neg | 37.1 |
| 8056G | Neg | Neg |
| 7477G | Neg | Neg |
| 9294H | 35.1 | 37.6 |
| 9496G | Neg | Neg |
| 5308G | Neg | Neg |

Neg=negative for target

The results from Table 5 showed that RNA can also be used as an assay target in addition to DNA if a reverse transcription step is employed to generate cDNA. Further, *Coccidioides* was detected in several samples that had negative detection results in DNA. Thus, these results demonstrate that RNA detection of *Coccidioides* can be used in addition to, or in place of DNA detection of *Coccidioides*.

Another set of clinical specimens underwent the CocciDxQ assay using both DNA and RNA from each specimen, and the results are provided in Table 6:

TABLE 6

CocciDxQ assay for clinical specimens

| | DNA | | | | RNA | | | |
|---|---|---|---|---|---|---|---|---|
| | Comparison real-time assays to ITS | | Control real-time PCR | | Comparison real-time assays to ITS | | Comparison real-time assays to ITS | |
| Sample Name | CDxQ | CQBD | 16S | ALU | CDxQ | CQBD | 16S | ALU |
| TG004-2_saliva | Neg | Neg | 30.7 | NR | Neg | Neg | 21.0 | 25.4 |
| TG006_saliva | Neg | Neg | 31.5 | 19.6 | Neg | Neg | 26.2 | 22.3 |
| TG006-2_saliva | Neg | Neg | 28.7 | 20.7 | Neg | Neg | 25.9 | 23.7 |
| TG009_saliva | Neg | Neg | 29.9 | 17.6 | Neg | Neg | 22.2 | 20.0 |
| TG009-2_saliva | Neg | Neg | 26.1 | 20.5 | Neg | Neg | 24.4 | 7.3 |
| TG010_saliva | Neg | Neg | 31.3 | 21.0 | Neg | Neg | 23.7 | 20.1 |
| TG010-2_saliva | Neg | Neg | 32.1 | 21.0 | Neg | Neg | 27.1 | 18.8 |
| TG010-2_sputum | Neg | Neg | 32.1 | NR | Neg | Neg | 31.6 | 16.1 |
| TG011_sputum | Neg | Neg | 24.4 | NR | Neg | Neg | 25.0 | 18.4 |
| TG012_saliva | Neg | Neg | 31.7 | 21.6 | Neg | Neg | 29.2 | 24.7 |
| TG012-2_saliva | Neg | Neg | 31.8 | 17.3 | Neg | Neg | 28.7 | 19.6 |
| TG012-2_sputum | Neg | Neg | 28.7 | NR | Neg | Neg | Neg | 31.7 |
| TG012-3_saliva | Neg | Neg | 31.8 | 20.3 | Neg | Neg | 27.6 | 21.2 |
| TG013_sputum | 38.2 | Neg | 30.8 | 26.4 | 27.8 | Neg | 28.3 | 19.0 |
| TG013_saliva | Neg | Neg | 24.4 | NR | Neg | Neg | 24.8 | 19.0 |
| TG013_sputum | Neg | Neg | 24.4 | NR | 36.9 | Neg | 16.2 | 12.9 |
| TG014_saliva | Neg | Neg | 31.9 | NR | Neg | Neg | 27.9 | 34.4 |
| TG015_saliva | Neg | Neg | 30.8 | 21.0 | Neg | Neg | 25.3 | 21.6 |
| TG015-2_sputum | Neg | Neg | 23.7 | NR | Neg | Neg | 21.5 | 24.8 |

TABLE 6-continued

CocciDxQ assay for clinical specimens

| | DNA | | | | RNA | | | |
|---|---|---|---|---|---|---|---|---|
| | Comparison real-time assays to ITS | | Control real-time PCR | | Comparison real-time assays to ITS | | Comparison real-time assays to ITS | |
| Sample Name | CDxQ | CQBD | 16S | ALU | CDxQ | CQBD | 16S | ALU |
| TG016_sputum | Neg | Neg | 21.6 | NR | Neg | Neg | 16.4 | 12.8 |
| PC (DNA only) | 17.3 | 20.4 | 9.9 | NR | NR | NR | NR | NR |

We claim:

1. A method of determining the presence or absence of *Coccidioides* in a DNA-containing sample comprising the steps of:
adding a first and a second oligonucleotide capable of binding SEQ ID NO. 1 to a mixture comprising the DNA-containing sample, wherein the first oligonucleotide includes at least one sequence selected from the group consisting of SEQ ID NO. 3, SEQ ID NO. 4, SEQ ID NO. 5 and oligonucleotides having at least 90% sequence identity to any one of SEQ ID NOs: 3-5, wherein the second oligonucleotide includes at least one sequence selected from the group consisting of SEQ ID NO. 6, SEQ ID NO. 7, SEQ ID NO. 8, SEQ ID NO. 9, and oligonucleotides having at least 90% sequence identity to any one of SEQ ID NOs: 6-9;
subjecting the mixture containing the first and second oligonucleotides to conditions that allow amplification of nucleic acid comprising the first oligonucleotide;
obtaining a result indicating nucleic acid amplification comprising the first oligonucleotide; and
determining the presence or absence of *Coccidioides* in the DNA-containing sample based on the result.

2. The method of claim 1, wherein the result comprises a Ct value.

3. The method of claim 1, wherein the first oligonucleotide is capable of hybridizing with complements of SEQ ID NO. 3, and the second oligonucleotide is capable of hybridizing with complements of SEQ ID NO. 6 in the mixture.

4. The method of claim 1, further comprising the step of adding a third oligonucleotide to the mixture, wherein the third oligonucleotide binds to its complement included in the amplification products by the first and second oligonucleotides.

5. The method of claim 4, wherein the third oligonucleotide includes a sequence selected from the group consisting of SEQ ID NO. 2 and oligonucleotides having at least 90% sequence identity to SEQ ID NO. 2.

6. The method of claim 4, wherein at least one of the first, the second and the third oligonucleotides comprises a label.

7. The method of claim 6, wherein the label comprises a fluorescent label.

8. The methods of claim 6, wherein the third oligonucleotide comprises a fluorescent label.

9. The method of claim 1, further comprising the step of isolating DNA from the DNA-containing sample.

10. The method of claim 1, wherein the sample comprises an environmental sample.

11. The method of claim 1, wherein the sample comprises a biological sample.

12. The method of claim 1, wherein the sample is derived from a subject.

13. The method of claim 12, wherein the subject is selected from the group consisting of a human, a companion animal, a domesticated animal, a livestock animal, and a wild animal species.

14. A method of quantifying *Coccidioides* in a DNA-containing sample comprising the steps of:

adding a first and a second oligonucleotides capable of binding SEQ ID NO. 1 to a mixture comprising the DNA-containing sample, wherein the first oligonucleotide includes a sequence selected from the group consisting of SEQ ID NO. 3, SEQ ID NO. 4, SEQ ID NO. 5and oligonucleotides having at least 90% sequence identity to any one of SEQ ID NOs: 3-5, wherein the second oligonucleotide includes a sequence selected from the group consisting of SEQ ID NO. 6, SEQ ID NO. 7, SEQ ID NO. 8, SEQ ID NO. 9, and oligonucleotides having at least 90% sequence identity to any one of SEQ ID NOs: 6-9;

subjecting the mixture containing the first and second oligonucleotides to conditions that allow amplification of a template DNA comprising the first oligonucleotide;

obtaining a first result indicating amplification of the template DNA and *Coccidioides* quantification; and calculating *Coccidioides* quantification based on the first result in comparison to a reference result, wherein *Coccidioides* quantification determines the amount of template DNA in the sample.

15. The method of claim 14, wherein the reference result is obtained by amplification of a DNA-containing sample having a known quantity of *Coccidioides*.

16. The method of claim 14, wherein the reference result is predetermined.

17. The method of claim 14, wherein the first and the reference result each comprises a Ct value.

18. The method of claim 14, wherein the first oligonucleotide is capable of hybridizing with complements of SEQ ID NO. 3, and the second oligonucleotide is capable of hybridizing with complements of SEQ ID NO. 6in the mixture.

19. The method of claim 14, further comprising the step of adding a third oligonucleotide to the mixture, wherein the third oligonucleotide binds to its complement included in the amplification products by the first and second oligonucleotides.

20. The method of claim 19, wherein the third oligonucleotide includes a sequence selected from the group consisting of SEQ ID NO. 2 and oligonucleotides having at least 90% sequence identity to SEQ ID NO. 2.

21. The method of claim 19, wherein at least one of the first, the second, and the third oligonucleotides comprises a label.

22. The method of claim 21, wherein the label comprises a fluorescent label.

23. The method of claim 21, wherein the third oligonucleotide comprises a fluorescent label.

24. The method of claim 14, further comprising the step of isolating DNA from the DNA-containing sample.

25. The method of claim 14, wherein the sample comprises an environmental sample.

26. The method of claim 14, wherein the sample is derived from a subject.

27. The method of claim 26, wherein the subject is selected from the group consisting of a human, a companion animal, a domesticated animal, a livestock animal, and a wild animal species.

* * * * *